United States Patent [19]

Jakobsen et al.

[11] Patent Number: 5,536,721
[45] Date of Patent: Jul. 16, 1996

[54] THIENO[2,3-B-INDOLE DERIVATIVES AND THEIR USE FOR TREATING CENTRAL NERVOUS SYSTEM DISEASES RELATED TO THE METABOTROPIC GLUTAMATE RECEPTOR SYSTEM

[75] Inventors: Palle Jakobsen, Væløse; Anders Kanstrup, Virum; Peter Faarup, Væerløse; Preben H. Olesen, København NV, all of Denmark

[73] Assignee: Novo Nordisk A/S, Bagsvaerd, Denmark

[21] Appl. No.: 403,357

[22] Filed: Mar. 14, 1995

[30] Foreign Application Priority Data

Mar. 14, 1994 [DK] Denmark .................................. 0295/94

[51] Int. Cl.$^6$ ...................... C07D 495/04; C07D 413/06; A61K 31/40; A61K 31/535
[52] U.S. Cl. .................... 514/232.8; 514/228.2; 514/252; 514/261; 514/262; 514/263; 514/364; 514/382; 514/411; 544/60; 544/142; 544/372; 548/127; 548/128; 548/134; 548/136; 548/131; 548/252; 548/430
[58] Field of Search ............................ 548/430; 514/411, 514/232.8; 544/142

[56] References Cited

FOREIGN PATENT DOCUMENTS 4736757  9/1972  Japan .

OTHER PUBLICATIONS

Kenji Kanbe et al. Biosci. Biotech. Biochem., 57(4) 632–635 Apr. 1993.
Chemical Abstracts 140005v vol. 77 (5)1972.

Primary Examiner—Johann Richter
Assistant Examiner—Laura L. Stockton
Attorney, Agent, or Firm—Steve T. Zelson; Elias J. Lambiris

[57] ABSTRACT

The present invention relates to therapeutically active heterocyclic compounds, a method of preparing the same and to pharmaceutical compositions comprising the compounds. The novel compounds are useful in treating diseases in the central nervous system related to the metabotropic glutamate receptor system.

23 Claims, No Drawings

THIENO[2,3-B-INDOLE DERIVATIVES AND THEIR USE FOR TREATING CENTRAL NERVOUS SYSTEM DISEASES RELATED TO THE METABOTROPIC GLUTAMATE RECEPTOR SYSTEM

The present invention relates to therapeutic active thieno [2,3-b]indoles, a method for preparing the same, pharmaceutical compositions comprising the compounds and a method of treating therewith.

Recent molecular biological studies have clearly established the existence of two major types of glutamate receptors in the central nervous system namely the ionotropic and the metabotropic glutamate receptors. The latter is characterised by being G-protein-linked to changes in second messenger formation and modulation of ion channel function, (Meldrum, B. (1991) Epilepsy Res. 10, 55–61, Chapman, A. (1991) in Excitatory Amino Acids p. 265–286, Blackwell scientific publ. ltd., Oxford).

At present 6 different subtypes of the metabotropic glutamate receptors are described ($MGluR_1$ to $MGluR_6$) and in addition some spliced variants of the subtypes are reported.

The metabotropic glutamate receptor subtypes $MGluR_1$ and $MGluR_5$ are coupled to phosphoinositide hydrolysis (Johnson, G. and Bigge, C. F. (1991) Annu. Rep. Med. Chem. 26, 11–22, Hansen, J. J. and KrogsgaardLarsen, P. Med. Res. Rev. 10,55–94, Thomsen, C. and Suzdak, P. (1993) Eur. J. Pharmacol. 245, 299), while the others are coupled to cyclic AMP formation (Schoepp, D. D., Johnson, B. G. and Monn, J. A. (1992) J. Neurochem. 58, 1184–1186, Cartmell et al. (1992) J. Neurochem. 58, 1964–1966, Manzoni, O. et al. (1992) Eur. J. Pharmacol. 225, 357–358).

Compounds such as L-glutamate, quisqualate and ibotenate are known to act as non-selective agonists on the metabotropic glutamate receptors, while selective ionotropic glutamate receptor agonists such as NMDA, AMPA and kainate do have little effect on these receptors.

Recently a few compounds without activity at the ionotropic glutamate receptors but with activity at the metabotropic receptors have been identified.

These comprise trans-ACPD (trans 1S,3R-1-aminocyclopentane-1,3-dicarboxylic acid), the partial agonist L-AP3 (L-2-amino-3-phosphonopropionic acid) (Palmer, E., Monaghan, D. T. and Cotman, C. W. (1989) Eur. J. Pharmacol. 166, 585–587, Desai, M. A. and Conn, P. J. (1990) Neurosci. Lett. 109, 157–162, Schoepp, D. D. et al. (1991), J. Neurochem. 56, 1789–1796, Schoepp D. D. and Johnson B. G. (1989), J. Neurochem. 53, 1865–1613), L-AP4 (L-2-amino-4-phosphonobutyrate) which is an agonist at the $MGluR_4$ receptor (Thomsen C. et al. (1992), Eur. J. Pharmacol. 227, 361–362) and some of the isomers of CCG (2-(carboxycyclopropyl)glycines) especially L-CCG-I and L-CCG-II (Hayashi, Y. et al. (1992), Br. J. Pharmacol. 107, 539–543).

Very few selective antagonists at the metabotropic glutamate receptors have been reported, however some phenylglycine derivatives S-CPG (S-4-carboxyphenyl glycine), S-4C3HPG (S-4-carboxy-3-hydroxyphenyl glycine) and S-MCPG (S-alpha methyl-4-carboxyphenyl glycine) have been reported to antagonise trans ACPD stimulated phosphoinositide hydrolysis and thus possibly acting as antagonists at the metabotropic glutamate receptors at the subtypes $MGluR_1$ and $MGluR_5$ (Thomsen, C. and Suzdak, P, (1993) Eur. J. Pharmacol. 245, 299).

Literature evidence suggests that compounds selective for the metabotropic glutamate receptors either as agonists or antagonists are useful in the treatment of different neurological diseases.

The use of compounds active at the metabotropic glutamate receptors for the treatment of epilepsy is corroborated by investigations of the influence of trans-ACPD in the formation of convulsions (Sacaan and Schoepp, (1992), Neurosci. lett. 139, 77) and that phosphoinositide hydrolysis mediated via MGluR is increased after kindling experiments in rats (Akiyama et al. (1992),Brain Res. 569, 71).

Trans-ACPD has been shown to increase release of dopamine in the rat brain which indicates that compounds acting on the metabotropic glutamate receptors might be usable for the treatment of Parkinson's disease and Huntington's Chorea (Sacaan et al. (1992), J. Neurochem. 59, 245).

The use of compounds active at the metabotropic glutamate receptors for treatment of neurological diseases such as senile dementia has been indicated by the findings of Zheng and Gallagher ((1992), Neuron 9, 163) and Bashir et al. ((1993), Nature 363, 347) who demonstrated that activation of metabotropic glutamate receptors are necessary for the induction of long term potentiation (LTP) in nerve cells (septal nucleus,hippocampus) and the finding that long term depression is induced after activation of metabotropic glutamate receptors in cerebellar granule cells (Linden et al. (1991), Neuron 7,81).

Investigations also show that in the treatment of deficiencies of mental and motoric performance seen after conditions of brain ischemia the metabotropic glutamate receptor active compounds may prove usable.

Trans-ACPD has been shown to be a neuroprotective agent in an MCAO model in mice (Chiamulera et al. (1992), Eur. J. Pharmacol. 215, 353), and it has been shown to inhibit NMDA induced neurotoxicity in nerve cell cultures (Koh et al., (1991), Proc. Natl. Acad. Sci. USA 88, 9431).

Also in the treatment of pain the metabotropic glutamate receptor active compounds seem of interest, proved by the fact that antagonists at the metabotropic glutamate receptors antagonises sensory synaptic response to noxious stimuli of thalamic neurons (Eaton, S. A. et al. (1993), Eur. J. Neurosci. 5, 186).

The above findings support that compounds acting on the metabotropic glutamate receptors are useful for the treatment of epilepsy, neurological diseases such as senile dementia, Parkinson's disease, Huntington's Chorea, pain and deficiencies of mental and motoric performance seen after conditions of brain ischemia.

We have now discovered a series of new thieno[2,3-b] indoles which are potent antagonists at the metabotropic glutamate receptors.

The present invention relates to compounds of formula I

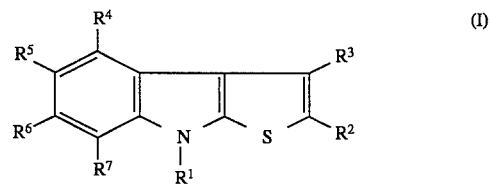

wherein $R^1$ is H, $C_{1-6}$-alkyl optionally substituted with halogen, $C_{2-6}$-alkenyl, $C_{2-6}$-alkynyl, $C_{3-6}$-cycloalkyl, $C_{1-4}$-alkyl substituted with $C_{3-6}$-cycloalkyl, carboxy,—$COR^9$, —$COR^9$, $C_{1-4}$-alkyl substituted with dimethylamino,—$R^9$—O—$R^{10}$, —$R^9$—O—$R^{11}$, phenylsulfonyl,.benzoyl, benzyl or phenyl each of which aromatic group is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl;

$R^2$ is H, carboxy, cyano, nitro, $C_{1-6}$-alkyl optionally substituted with hydroxy, —$R^9$—O—$R^{10}$, —$COOR^9$, morpholinocarbonyl, thiamorpholinocarbonyl, piperazinylcarbonyl optionally substituted with $C_{1-4}$-alkyl, tetrazolyl, oxadiazolyl or thiadiazolyl optionally substituted with $C_{1-4}$-alkyl or $C_{3-6}$-cycloalkyl, morpholinomethyl, amino unsubstituted or mono or disubstituted with $C_{1-6}$-alkyl, methylamino unsubstituted or N-mono or disubstituted with $C_{1-6}$-alkyl, sulfamoyl unsubstituted or mono or disubstituted with $C_{1-6}$-alkyl or carbamoyl unsubstituted or mono or disubstituted with $C_{1-6}$-alkyl which alkyl group(s)is/are independently optionally substituted with dimethylaminomethyl, halogen, phenyl or benzyl;

$R^3$ is H, $C_{1-6}$-alkyl, trifluoromethyl, trifluoroacetyl, $C_{1-6}$-alkoxy, halogen, nitro, cyano, —$COOR^9$ or amino unsubstituted or mono or disubstituted with $C_{1-6}$-alkyl;

$R^4$, $R^5$, $R^6$ and $R^7$ are independently H, nitro, amino, halogen, tritium, trifluoromethyl, trifluoroacetyl, sulfo, carboxy, carbamoyl, sulfamoyl, —$COR^9$, —$COOR^9$, $C_{1-6}$-alkoxy, $C_{1-6}$-alkyl optionally substituted with halogen;

or a salt thereof with a pharmaceutically acceptable acid or base.

Alkyl, alkenyl and alkynyl are intended to mean a straight or branched alkyl, alkenyl or alkynyl chain.

These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The invention also relates to a method of preparing the above mentioned compounds. These methods comprise a) reacting a compound of formula II

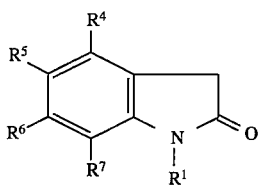

prepared by well-known methods, wherein $R^1$, $R^4$, $R^5$, $R^6$ and $R^7$ have the meanings defined above, with an N,N-dimethyl amide, preferably formamide, and $POCl_3$ using Vilsmeyer-Hack conditions, to form a compound of formula III

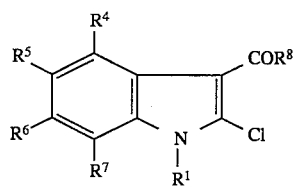

wherein $R^8$ is H or methyl and $R^1$, $R^4$, $R^5$, $R^6$ and $R^7$ have the meanings defined above; and subsequently b) reacting a compound of formula III wherein $R^1$, $R^4$, $R^5$, $R^6$, $R^7$ and $R^8$ have the meanings defined above with methyl mercaptoacetate to form a compound of formula IV

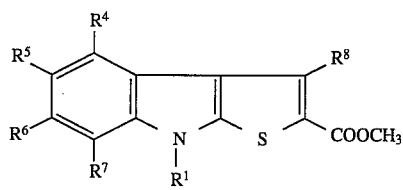

wherein $R^1$, $R^4$, $R^5$, $R^6$, $R^7$ and $R^8$ have the meanings defined above; and subsequently c) reacting a compound of the formula IV wherein $R^1$, $R^4$, $R^5$, $R^6$, $R^7$ and $R^8$ have the meanings defined above by means of well-known chemical reactions transforming the methylester group to other functional groups such as acids, esters, amides, amines or reaction products thereof as described for the $R^2$ substituent, to form a compound of formula I wherein $R^1$, $R^2$, $R^4$, $R^5$, $R^6$ and $R^7$ have the meanings defined above and $R^3$ is H or methyl; or d) reacting a compound of formula I

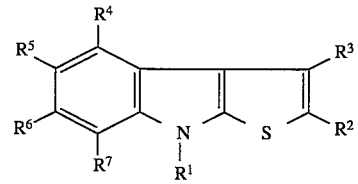

wherein $R^1$ is H and $R^2$, $R^3$, $R^4$, $R^5$, $R^6$ and $R^7$ have the meanings defined above with $R^1$-Y wherein $R^1$ has the meaning defined above and Y is a leaving group such as halogen or sulphonate, using strong base as e.g. metal hydrides to form a compound of formula I wherein $R^1$, $R^2$, $R^3$, $R^4$, $R^5$, $R^6$ and $R^7$ have the meanings defined above provided that $R^1$ is not H; or e) reacting a compound of the formula III

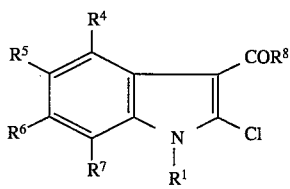

wherein $R^1$ is H and $R^4$, $R^5$, $R^6$, $R^7$ and $R^8$ have the meanings defined above with a compound $R^1$-Y wherein Y is a leaving group such as e.g. halogen or sulphonate, using strong base such as e.g. metalhydrides to form a compound of formula III wherein $R^1$, $R^4$, $R^5$, $R^6$, $R^7$ and $R^8$ have the meanings defined above provided that $R^1$ is not H; or f) reacting a compound of formula I wherein $R^1$, $R^2$ and $R^3$ have the meanings defined above and at least one of $R^4$, $R^5$, $R^6$ or $R^7$ is H with well known reactive substrates leading to aromatic substitution using the reaction conditions known in the art, to form a compound of formula I wherein $R^4$, $R^5$, $R^6$ and $R^7$ have the meanings defined above provided that at least one of $R^4$, $R^5$, $R^6$ or $R^7$ is not H; or g) a compound of formula I with different $R^4$, $R^5$, $R^6$ and $R^7$ groups could be prepared by using conventional organic chemistry on functional groups already introduced as $R^4$, $R^5$, $R^6$ and $R^7$ groups.

The pharmacological properties of the compounds of the invention can be illustrated by determining their effects in different conventional radioligand binding assays or in functional in vitro assays.

The compounds of the invention were studied in an in vitro assay for measuring inhibition of PI-hydrolysis in BHK 570 cells expressing mGluR$_1\alpha$ receptors.

Principle

The metabotropic glutamate receptor (mGluR) is selectively activated by trans-aminocyclopentane dicarboxylic acid and is coupled to the hydrolysis of inositol phosphates via a GTP-binding protein. At the molecular level, cDNAs encoding six subtypes of the mGluR family have been isolated. The first subtype isolated (Houamed et al., 1991, Science 252, 1318), termed the mGluR1$\alpha$, has been shown to be coupled to PI-hydrolysis when expressed in baby hamster kidney cells (BHK) (Thomsen et al., Brain Res. (in press)). In these cells no stimulation by 1 mM quisqualate or glutamate was observed with control BHK cells whereas a 6–8 fold increase over basal PI-hydrolysis was seen with BHK cells expressing mGluR1$\alpha$.

Cell culture

BHK570 cells expressing mGluR1$\alpha$ are cultured in DMEM (4.5 g/l glucose, 2ram glutamin); 5% foetal calf serum; 0.10 mg/ml neomycin; 0.5 mg/ml G418; 1 µM methotrexate; 50 pg/ml gentamycin. Cells are subcultured every 5 days using 0.05% trypsin/EDTA in PBS.

Inositol phosphate formation

The protocol for PI-hydrolysis was measured using a modification of a method previously described (Berridge et al., 1982, Biochem. J. 206,587). Cells were plated in 16 mm wells (24 well multidish, Costar) with 1 confluent 100 mm dish per multidish. Replace the medium 24 h before the experiment with 500 µl fresh growth medium containing 4µCi/ml myo-[2-$^3$H]inositol (specific activity 18 Ci/mmol, Amersham). The cells were washed twice with Krebs-Henseleit buffer (Sigma cat.#3753: glucose 2.0 g/l, MgSO$_4$ 0.141 g/l, KHPO$_4$0.16 g/l, KCl 0.35 g/l, NaCl 6.90 g/l and NaHCO$_3$2.1 g/l) supplemented with 10 mM LiCl and 2.5 mM CaCl$_2$. The buffer was equilibrated with 5% CO$_2$, 95% air to pH 7.5 at 37° C. Following 5 min of preincubation in the above buffer, buffer or test compounds were added and cells were incubated for 30 rain at 37° C. In antagonist studies, add test compounds 5 min prior to agonist stimulation. PI-formation was stopped by placing the cells on ice and quickly aspirating the media. The wells were washed once with ice-cold Krebs-Henseleit buffer and subsequently 1 ml ice-cold 10% perchloric acid was added to each well. Place the cells on ice for 20 min. In Nunc minisorp test tubes (75 ×12 mm, cat. #443990): add 250 µl of 10 mM EDTA, pH 7.0+5% Universal Indicator (Merck). Transfer the PCA extract to each tube containing the pH-indicator. Neutralize the samples with 1.5M KOH+60 mM HEPES to pH 7.5 (~1100–1200 µl). Centrifugate (6.000 rpm, 5 min, 0° C.). They can be stored frozen at this point. Fractions of inositolphosphates were separated using ion-exchange columns (Amersham, RPN 1908) according to the method provided by Amersham.

Separation of inositol phosphates on ion-exchange columns

Prepare columns with 5 ml 1M KHCO$_3$ and wash with 15 ml dist. water. Adjust vacuum so that the flow-rate does not exceed 5 ml/min. Add 4 ml dist. water and subsequently 1 ml [$^3$H]InsP sample. Wash with 5 ml dist. water. IP1 to IP4 fractions may be collected with 5 ml 0.05; 0.10; 0.17 and 0.25M KHCO$_3$, respectively. Usually IP1 and IP2 fractions are collected simultaneously. Scintillation liquid: use 12–15 ml Ultima Gold (Packard).

Testprocedure

Testcompounds are dissolved in DMSO, DMSO and Pluronic F-127 or ethanol and diluted in assay buffer. Glutamate (10 µM and 1000 µM) and buffer alone are included as a control.

Results

The stimulation by 10 µM shall represent a submaximal stimulation. The response by 10 µM glutamate should exceed 3-fold the basal level and should be below maximal stimulation (glutamate at 1 mM). The results are calculated relative to be stimulation by 10 µM glutamate and a dose response curve is generated.

Examples of test results obtained by testing some compounds of the present invention in the above mentioned assay appear from the following Table 1.

TABLE 1

| Compound No. | IC$_{50}$ (uM) |
| --- | --- |
| 27 | 5.3 |
| 8 | 21.0 |
| 54 | 7.2 |
| 31 | 36.0 |
| 25 | 9.0 |

The compounds according to the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from a disease in the central nervous system related to the metabotropic glutamate receptor system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, topical, intramuscular, intranasal, ophthalmic solution or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph.Eur. |
| Avicel ® | 31.4 mg |
| Amberlite ® | 1.0 mg |
| *Magnesii stearas* | 0.25 mg Ph. Eur. |

The invention will now be described in further detail with reference to the following examples.

EXAMPLE 1

2-Chloroindole-3-carbaldehyde (1)

$POCl_3$ (100 ml) was added dropwise to a mixture of dry DMF (100 ml) and dichloromethane (100 ml) kept at 0° C. Indolone (50 g) dissolved in dichloromethane (200 ml) and pyridine (50 ml) was added dropwise at 0° C. over a period of 1.5 h. Subsequent stirring at 0° C. for 1 h. The mixture was poured onto icewater (2000 ml) neutralised with $NaHCO_3$ whereafter the mixture was stirred overnight. The aqueous phase was decanted and the organic phase evaporated followed by extraction with ethanol (boiling). The ethanolic phase was evaporated and the crystalline residue recrystallized from ethanol yielding 70 g of (1), m.p. 227° C.

1-Benzyl-2-chloroindole-3-carbaldehyde (2)

(1) (10 g) was added to a slurry of NaH (2.7 g) in dry DMF (100 ml), subsequently benzyl bromide (9.52 g) was added to the mixture and stirring was continued at RT overnight. Benzyl bromide (2.9 g) was added and stirring was continued for 4 h. The mixture was poured on water (100 ml) and extracted three times with ether. The water phase was further extracted two times with ether followed by a filtration of the water phase. The crystals isolated by filtration of the water phase and the crystals isolated by evaporation of the two last ether extractions were mixed giving (2) (9.2 g), m.p. 136.5°–137.5° C.

In the same way the following 1-substituted 2-chloroindole-3-carbaldehydes were prepared.

1-Methyl-2-chloroindole-3-carbaldehyde (3)

Prepared from (1) (18 g), methyl iodide (17.1 g) and NaH (2.88 g) yielding (3) (18.2 g), m.p. 88°–90° C.

1-Cyclopropylmethyl-2-chloroindole-3-carbaldehyde (4)

Prepared from (1) (18 g), cyclopropylmethyl bromide (16.2 g) and NaH (2.8 g) yielding (4) (23 g), m.p. 108°–109° C.

In this reaction THF was used as solvent in stead of DMF and the reaction mixture was partly evaporated before treatment with water.

EXAMPLE 2

Methyl 8-benzylthieno[2,3-b]indole-2-carboxylate (5)

(2) (9.2 g)dissolved in methanol (100 ml) and $K_2CO_3$(10.2 g) were mixed, methyl 2-mercapto acetate (4.7 g) was added and the mixture was stirred overnight. Water (100 ml) was added and the mixture stirred for further 2 h. The mixture was then filtered and the precipitate rinsed thoroughly with water and dried in vacuo at 100° C. giving (5) (10 g) as slight pink crystals, m.p. 158.3°–158.8° C.

The following thieno[2,3-b]indolecarboxylates were prepared in the same way:

Methyl 8-methylthieno[2,3-b]indole-2-carboxylate (6)

Prepared from (3) (9.6 g), $K_2CO_3$ (15 g) and methyl 2-mercaptoacetate (10 ml) yielding (6) (9.3 g), m.p. 133.5°–133.8° C.

Methyl 8-cyclopropylmethylthieno[2,3-b]indole-2-carboxylate (7)

Prepared from (4) (6.5 g), $K_2CO_3$ (10 g) and methyl 2-mercaptoacetate (3.2 ml) yielding (7) (6 g), m.p. 110°–111° C.

EXAMPLE 3

8-Benzylthieno[2,3-b]indole-2-carboxylic acid (8)

KOH (3 g) was dissolved in methanol-water (1/1) (50 ml). (5) (3 g) was added and the mixture refluxed until the compound was in solution and subsequently 1 h in addition. After cooling the mixture was acidified with acetic acid to pH=6, and the mixture was stirred overnight. The formed precipitate was filtered off, washed with water and dried in vacuo at 50° C. The crude product (3 g) was boiled in water once more, cooled, filtered and dried again giving analytically pure (8), m.p. 194–195° C.

In the same way the following thieno[2,3-b]indole-2-carboxylic acids were prepared:

8-Methylthieno[2,3-b]indole-2-carboxylic acid (9)

Prepared from (6) (2.1 g) after reflux for 3 h yielding (9) (1.9 g) after rinse up, m.p. 179°–180° C.

EXAMPLE 4

8-Benzylthieno[2,3-b]indole-2-carbonyl chloride (10)

(8) (1 g) was dissolved in $SOCl_2$ (20 ml) and the mixture was stirred overnight at RT. The mixture was subsequently evaporated to dryness, the residue treated with acetone resulting in a small amount of colourless residue which was filtered off. The filtrate was evaporated to dryness resulting in dark purple crystals which are used for further reactions without additional rinse up. Yielding (10) (0.95 g).

8-Benzylthieno[2,3-b]indole-2-carboxamide (11)

(10) 0.5 g was dissolved in acetone. An aqueous solution of $NH_3$ (25%, 3 ml) was added and the mixture was stirred at RT for 1 h. Water was added resulting in precipitation. After further 0.5 h stirring the precipitate was filtered off washed with water and dried in vacuo yielding 0.47 g (11), m.p. 206.7°–207.3° C.

8-Benzylthieno[2,3-b]indole-2-(N',N'-dimethyl-3-aminopropyl)-N-(12)

(10) (0.45 g) was reacted with 3-dimethylaminopropaneamine (0.17 g) in acetone by stirring overnight at RT. By addition of water to the reaction mixture a brownish oil separated. The oil was treated with pentane resulting in brown hygroscopic crystals. Reprecipitation from methanol/acetone/pentane gave 0.34 g crystals corresponding to the dihydrate of (12) according to the elemental analysis, m.p. 212.2–214.0° C.

8-Benzyl-2-(4-methyl-1-piperazinylcarbonyl)thieno[2,3-b]indole (13)

(10) (0.5 g) and 4-methylpiperazine (0.3 g) were stirred in acetone (50 ml) overnight. Treatment with water resulted in an oil. The mixture was extracted three times with ether, the etheral layers dried with $MgSO_4$ filtered and evaporated to dryness. The resulting crude (13) (0.55 g) was recrystallised from acetone-pentane and subsequently precipitated as the hydrochloride from acetone solution, m.p. 222°–224° C.

8-Benzylthieno[2,3-b]indole-2-(N-dimethylaminopropyl-N-methylcarboxamide) (14)

(10) (0.5 g) and N-methyl-3-dimethylaminopropaneamine (0.2 g) were stirred in acetone at RT for 2 days. The mixture was evaporated and subsequently purified on a silica gel column using dichloromethane/methanol (4/1) as eluent. After evaporation of solvent and precipitation as the hydrochloride from acetone/methanol/pentane (0.4 g) (14) was isolated, m.p. 172°–174° C.

8-Benzyl-2-morpholinocarbonylthieno[2,3-b]indole (15)

(10) (1.6 g) was heated to 80° C. together with morpholine (2 ml) in dry toluene. The mixture was cooled resulting in precipitation of (15) (1.5 g), m.p. 199°–201° C.

8-Benzylthieno[2,3-b]indole-2-N-ethylcarboxamide (16)

(10) (1 g) was treated with ethylamine hydrochloride (3 g) in toluene (30 ml), triethylamine (4 ml) was added and the mixture heated to 80° C. for 0.5 h. Cooling followed by filtration resulted in (16) (0.85 g), m.p. 175°–176° C.

8-Benzyl-2-(3-cyclopropyl-1,2,4-oxadiazol-5-yl)thieno[2,3-b]indole (17)

(8) (2 g) was treated with $SOCl_2$ (10 ml) by stirring at RT for 1 min. Excess $SOCl_2$ was evaporated and toluene (40 ml) followed by cyclopropylamide oxime (1.5 g) and triethylamine (2 ml) were added. Stirring at RT for 0.5 h followed by heating for 0.5 h at 80° C. resulted in a precipitate which was filtered off and treated with dry xylene (30 ml) by heating to 130° C. for 5 h. Evaporation to dryness gave an oil which after treatment with methanol gave (17) (1.5 g) as a crystalline compound, m.p. 140°–141° C.

Isopropyl 8-benzylthieno[2,3-b]indole-2-carboxylate (18)

(5) (1 g) was mixed with titanium(IV)isopropoxide ((4 ml) and IPA (50 ml). Reflux for 6 h followed by evaporation of IPA and treatment with water and subsequent filtration resulted in a crystalline mass which was dried. Subsequent trituration with dichloromethane, isolation of organic phases, evaporation to dryness followed by trituration of the residue with petrol ether resulted in (18) (0.9 g), m.p. 88°–89° C.

EXAMPLE 5

Methyl thieno[2,3-b]indole-2-carboxylate (19)

(5) (4.5 g) was dissolved in toluene (150 ml) and aluminium chloride (9.35 g) was added and the mixture stirred at RT overnight. Methanol (50 ml) was added cautiously and after termination of the heat development the reaction mixture was evaporated and extracted with water/ethyl acetate twice. The organic phases dried with $MgSO_4$ and evaporated. The residue was treated with methanol filtered and the filtrate evaporated. Addition of a small amount of methanol resulted in precipitation of (19) (2.6 g), m.p. 200°–201° C.

Methyl 8-benzenesulphonylthieno[2,3-b]indole-2-carboxylate (20)

(19) (0.5 g) was added to a slurry of NaH (0.06 g)in dry THF. Benzenesulphonyl chloride (0.39 g) was added dropwise and the mixture stirred at RT overnight. Addition of water resulted in formation of a precipitate which was filtered off and dried, resulting in (20) (0.8 g), m.p. 195.1°–197.2° C.

Methyl 8-benzoylthieno[2,3-b]indole-2-carboxylate (21)

Prepared analogously to (20) from (19) (0.5 g), 0.06 g NaH and 0.46 g benzoyl chloride afforded (0.7 g)(21), m.p. 149.5°–151.2° C.

Methyl 8-acetylthieno[2,3-b]indole-2-carboxylate (22)

Preparation as described for (21) from (19) (0.5 g), acetyl chloride (0.17 g) and NaH (0.06 g) resulted in (22) (0.55 g), m.p. 179°–181° C.

2-Morpholinocarbonylthieno[2,3-b]indole (23)

(15) (0.5 g) was treated with $AlCl_3$ (1.5 g) as described for the preparation of (19). The product arising from the ethyl acetate extraction was purified on silica gel using ethyl acetate as eluent resulting in 0.2 g of (23), m.p. 92–95° C.

EXAMPLE 6

8-Benzylthieno[2,3-b]indole-2-carbonitrile (24)

(8) (3 g) was mixed with acetonitrile (100 ml) followed by addition of chlorosulphonyl isocyanate (1.62 g). The mixture was stirred overnight at RT whereafter triethyl amine (1.46 g) was added and the mixture stirred overnight at RT. The mixture was evaporated extracted three times with NaOH/ether, the combined etheral layers were evaporated followed by rinse up on silica gel using pentane/triethylamine (15/1) as eluent. The residue after evaporation of the eluent was treated with ether resulting in (24) (1.15 g), m.p. 130°–132° C.

8-Benzyl-2-(5-tetrazolyl)thieno[2,3-b]indole (25)

(24) (0.3 g)in chloroform (50 ml) was treated with $NaN_3$ (0.42 g) and $NH_4Cl$ (0.36 g) by stirring at reflux overnight. The mixture was evaporated followed by addition of water and acidifying with acetic acid resulting in preparation of yellow crystals (0.32 g). The crystals were purified on silica gel using dichloromethane/methanol (4/1) as eluent yielding 0.07 g pure (25), m.p. 277°–280° C. (decomp.).

EXAMPLE 7

8-Methylthieno[2,3-b]indole-2-carbonyl chloride (26)

Preparation as described for (10) from (9) (2.0 g) and 20 ml $SOCl_2$ gave 2.1 g (26) which was used without further purification.

8-Methyl-2-morpholinocarbonylthieno[2,3-b]indole (27)

(26) (0.7 g) was mixed with morpholine (0.29 g)in acetone (100 ml) and stirred at RT overnight. The reaction mixture was evaporated and treated with NaOH whereafter it was extracted with ether and subsequently dichloromethane. The organic phases were mixed and evaporated yielding an oil, which was purified on silica gel using dichloromethane/ether (1/1) as eluent. After evaporation of the eluent 0.35 g of (27) was isolated as brownish crystals, m.p. 125°–127° C.

8-Methylthieno[2,3-b]indole-2-(N-methylcarboxamide) (28)

Preparation as described for (27) from (26) (0.7 g) and methylamine (gas) which was bobbled through the acetone solution until a clear solution was obtained. Rinse up on column with dichloromethane/methanol (9/1) as eluent. After evaporation of eluent the residue was reprecipitated from acetone-pentane yielding (28) (0.36 g), m.p. 217°–219° C.

8-Methylthieno[2,3-b]indole-2-(N,N-dimethylcarboxamide) (29)

Preparation as described for (28) from (26) (0.7 g) and dimethylamine (gas). After termination of the addition of dimethyl amine the mixture was stirred at RT for 3 days. After rinse up on column and reprecipitation 0.44 g (29) was isolated, m.p. 151.5°–152.0° C.

8-Methylthieno[2,3-b]indole-2-(N-phenylcarboxamide) (30)

Preparation as described for (27) from (26) (0.96 g) and aniline (0.43 g), stirring at RT for 14 days. Reprecipitation from acetone-pentane gave (30) (0.45 g), m.p. 199.0°–199.4° C.

8-Methyl-2-(4-methyl-1-piperazinylcarbonyl)thieno[2,3-b]indole (31)

Preparation as for (30) from (26) (0.96 g) and N-methylpiperazine (0.46 g), stirring for 14 days, rinse up on silica gel column using dichloromethane/methanol (9/1) as eluent. Precipitation as the oxalate salt gave (31) (0.78 g), m.p. 219.1°–219.5° C.

8-Methyl-2-morpholinomethylthieno[2,3-b]indole (32)

(27) (0.8 g) was dissolved in THF (dry, 100 ml), $LiAlH_4$ (0.1 g) was added and the mixture stirred at RT for 1 h followed by reflux overnight. The reaction mixture was rinsed up using the normal procedure (water/NaOH). After filtration the filtrate was purified on silica gel using ethyl acetate/toluene (1/1) as eluent. 0.05 g (32) was isolated after precipitation and further 0.18 g by evaporation of the filtrate, m.p. 102.5°–106.0° C.

EXAMPLE 8

8-Benzyl-2-hydroxymethylthieno[2,3-b]indole (33)

(8) (0.9 g) was reduced with $LiAlH_4$ (1.2 g)in THF (50 ml) by stirring at RT overnight. After rinse up and filtration the filtrate was evaporated and purified on silica gel using ether as eluent. Precipitation from ether-pentane gave (33) (0.22 g), m.p. 81°–82° C.

Methyl 8-methyl-5-methoxythieno[2,3-b]indole-2-carboxylate (34)

5-Hydroxyindolone (0.87 g) dissolved in DMF (10 ml) was added to a solution of $POCl_3$ (20 ml), DMF (10 ml) and dichloromethane (10 ml) kept at 0° C. The reaction mixture was stirred at 0° C. for 1 h and subsequently at RT for 1 h. The mixture was then poured on water, neutralised with $NaHCO_3$ and stirred overnight, extraction with dichloromethane followed by purification on silica gel using $CH_2Cl_2/ CH_3OH$ (9/1) as eluent resulted in 0.4 g crystals. These were added slowly to a solution of NaH (0.12 g) in DMF (30 ml) followed by addition of methyl iodide (0.64 g). The mixture was stirred at RT overnight, water (100 ml) was added and the resulting mixture extracted with dichloromethane. The combined organic phases were dried with $MgSO_4$ and evaporated to dryness resulting in 0.27 g yellow crystals. These crystals were dissolved in methanol (50 ml), $K_2CO_3$ (0.35 g) and methyl mercaptoacetate (0.15 g) were added and the resulting mixture stirred overnight at RT. Water (100 ml) was added and the mixture stirred for 2 h followed by filtration. The resulting crystals were dried in vacuo yielding 0.2 g (34), m.p. 124°–125° C.

8-Benzylthieno[2,3-b]indole (35)

(8) (1.0 g) was heated for 2 h at 200° C. in quinoline (30 ml) with Cu (0.12 g) added. After cooling overnight the mixture was filtered, dichloromethane was added and the mixture extracted with dilute HCl and subsequently water.

The organic phase was dried (MgSO$_4$) and evaporated yielding brown crystals, which were recrystallised from ethanol/water (1/1) resulting in (35) (0.3 g) as slight grey crystals, m.p. 96°–98° C.

Ethyl 8-methylthieno[2,3-b]indole-2-carboxylate (36)

(6) (1 g), sodium ethoxide (0.5 g) and acetamide oxime (1 g) were refluxed together in ethanol (100 ml) to which crushed molecular sieves (0.5 g) was added. After reflux for 2 h and subsequent stirring at RT overnight the mixture was filtered and evaporated. Extraction with water/dichloromethane, followed by evaporation of the organic phases resulted in a crystalline mass which was rinsed on silica gel using dichloromethane as eluent. Yield 0.5 g of (36), m.p. 99°–100° C.

8-Methyl-2-(3-methyl-1,2,4-oxadiazol-5-yl)thieno[2,3-b]indole (37)

Repeating the procedure mentioned above for (36) using freshly prepared sodium ethoxide (from Na (0.26 g)in ethanol (50 ml)) and using reflux for 3 days followed by the same rinse up procedure as above, resulted in (37) (0.1 g), m.p. 199.8°–200.7° C.

Thieno[2,3-b]indole (38)

(23) (0.25 g) was heated to 110° C. in morpholine (3 ml) for 20 h. The mixture was poured on water, filtered and dried followed by rinse up on silica gel with dichloromethane as eluent, evaporation of the solvent resulted in (38) (0.05 g), m.p. 210°–211° C.

EXAMPLE 9

Methyl 8-benzyl-5-bromothieno[2,3-b]indole-2-carboxylate (39)

(5) (0.5 g) was dissolved in dichloromethane (30 ml), NBS (0.7 g) was added and the mixture stirred at RT for 0.5 h. Addition of water, separation of the organic phase which was subsequently washed with NaHCO$_3$ and dried with MgSO$_4$ and evaporated resulted in (39) (0.5 g), m.p. 134°–135° C.

8-Benzyl-5,6-dibromothieno[2,3-b]indole-2-carboxylic acid (40)

(5) (1 g) was treated with NBS (1.4 g) by stirring overnight at RT in CH$_2$Cl$_2$ (50 ml), filtration and evaporation resulted in 2 g of the methyl ester of (40) as yellow crystals which were washed with methanol, 0.5 g of these crystals were hydrolysed with KOH as described for (8) yielding 0.4 g of (40) after drying, m.p. 269°–273° C.

Methyl 5-bromothieno[2,3-b]indole-2-carboxylate (41)

Prepared from (39) (1 g) by means of AlCl$_3$ (2 g) as described for (19) gave 0.15 g of (41), m.p. 216°–218° C.

Thieno[2,3-b]indole-2-(N-ethylcarboxamide) (42)

Prepared from (16) (0.5 g) and AlCl$_3$ (1.5 g) as described above resulted in 0.2 g of (42), m.p. 253°–254° C.

EXAMPLE 10

1-Methyl-4,6-dichloro-1,3-dihydroindol-2-one (43)

1-Methyl-4,6-dichloroisatin (4.0 g) was suspended in dry ethanol (40 ml), hydrazine (9 ml) was added and the mixture was refluxed in 6 h. The mixture was then added slowly at 70° C. to a solution of sodium (1.74 g)in dry ethanol (80 ml) and refluxed overnight. The reaction mixture was cooled to room temperature, water (50 ml) was added and the volume was reduced to about one third by evaporation. The mixture was then poured onto icewater (1000 ml) and acidified with 6M HCl (pH=1). The precipitate was filtered off washed with water and dried to afford 3.27 g (87%) of (43). M.p. 144°–145° C.

In the same way 1-methyl-7-chloro-1,3-dihydroindol-2-one (44) was prepared from 1-methyl-7-chloroisatin (10 g), hydrazine (25 ml) and sodium (5.1 g) yielding 8.1 g (88%) of (44). M.p. 111°–113° C.

EXAMPLE 11

1-Methyl-2,5-dichloroindole-3-carbaldehyde (45)

POCl$_3$ (6 ml) was added dropwise to a mixture of dry DMF (5.9 ml) and dichloromethane (5.9 ml) kept at 0° C. 1-Methyl-5-chloro-1,3-dihydroindol-2-one (4.0 g) dissolved in dichloromethane (20 ml) and pyridine (2.9 ml) was added dropwise at 0° C. over a period of 30 min. Subsequent stirring at room temperature for 3h. The mixture was poured onto icewater (500 ml) neutralized with NaHCO$_3$ whereafter the mixture was stirred overnight. The precipitate was filtered off, washed with water and dried. The crude material (4.45 g) was recrystallized from ethanol yielding 1.27 g (25.4%) of (45). M.p. 165°–167° C.

In the same way the following substituted 2-chloroindole-3-carbaldehydes were prepared:

1,5-Dimethyl-2-chloroindole-3-carbaldehyde (46)

Prepared from POCl$_3$ (1.7 ml), DMF (1.6 ml), 1,5-dimethyl-1,3-dihydroindol-2-one (1.0 g) yielding (46) 1.0 g (78%). M.p. 120°–121° C. as crude product sufficiently pure for the next synthesis.

1-Methyl-2,7-dichloroindole-3-carbaldehyde (47)

Prepared from POCl$_3$ (17 ml), DMF (17 ml), (44) (7.5 g), yielding (47) 6.8 g (72%). M.p. 185°–187° C. In this reaction the reaction time was 48 h instead of 3 h.

1-Methyl-2,4,6-trichloroindole-3-carbaldehyde (48)

Prepared from POCl$_3$ (11 ml), DMF (11 ml), (43) (8.4 g), yielding (48) 6.5 g as crude product sufficiently pure for the next synthesis. $^1$H-NMR (DMSO-d$_6$): δ3.8 (s, 3H), 7.43 (d, 1H), 7.86 (d, 1H), 10.52 (s, 1H). In this reaction the reaction time was 24 h instead of 3 h.

EXAMPLE 12

Methyl 5-chloro-8-methylthieno[2,3-b]indole-2-carboxylate (49)

(45) (1.0 g) and K$_2$CO$_3$ (1.71 g) was suspended in methanol (20 ml), methyl 2-mercaptoacetate (0.68 ml) was added and the mixture stirred 2 h. Water (20 ml) was added and the mixture stirred for further 0.5 h. The precipitate was filtered off, washed with water and dried to give 1.04 g (85%) of (49). M.p. 188°–190° C. (recrystallized from methanol).

In the same way the following substituted thieno[2,3-b] indole-2carboxylates were prepared:

Methyl 7-chloro-8-methylthieno[2,3-b]indole-2-carboxylate (50)

Prepared from (47) (6.5 g), $K_2CO_3$ (11.17 g) and methyl 2-mercaptoacetate (4.46 ml) yielding (50) 6.62 g (83%). M.p. 166°–168° C.

Methyl 8-phenylthieno[2,3-b]indole-2-carboxylate (51)

Prepared from 1-Phenyl-2-chloroindole-3-carbaldehyde (0.90 g), $K_2CO_3$ (1.38 g) and methyl 2-mercaptoacetate (0.55 ml) yielding (51) 0.86 g (79.6%). M.p. 147°–149° C.

Methyl 5-methyl-8-methylthieno[2,3-b]indole-2-carboxylate (52)

Prepared from (46) (0.80 g), $K_2CO_3$ (1.5 g) and methyl 2-mercaptoacetate (0.60 ml) yielding (52) 0.144 g (14.4%). M.p. 152°–155° C.

Methyl 4,6-dichloro-8-methylthieno[2,3-b]indole-2-carboxylate (53)

Prepared from (48) (6.5 g), $K_2CO_3$ (9.59 g) and methyl 2-mercaptoacetate (3.82 ml) yielding (53) 2.5 g (32.5%). M.p. 231°–232° C. The product was purified by chromatography on silicagel using toluene as eluent. The compound was crystallized by trituration with methanol.

EXAMPLE 13

5-Chloro-8-methylthieno[2,3-b]indole-2-carboxylic acid (54)

KOH (0.57 g) was dissolved in methanol-water (1/1) (10 ml). (49) (0.50 g) was added and the mixture refluxed for 1¾ h. After cooling the mixture was acidified with 1M HCl to pH=1. The precipitate was filtered off, washed with water and dried to give 0.44 g (93%) of (54). M.p. 259°–262° C.

In the same way the following substituted thieno[2,3-b] indole-2-carboxylic acids were prepared, with the exception of that the reaction mixture was acidified with acetic acid to pH=5.

5-Methyl-8-methylthieno[2,3-b]indole-2-carboxylic acid (55)

Prepared from KOH (0.40 g), (52) (0.33 g) yielding (55) 0.312 g (100%). M.p. 216°–219° C.

4,6-Dichloro-8-methylthieno[2,3-b]indole-2-carboxylic acid (56)

Prepared from KOH (2.23 g), (53) (2.20 g) after reflux for 4⅓ h yielding (56) 1.67 g (79.5%). M.p. 278°–281° C.

7-Chloro-8-methylthieno[2,3-b]indole-2-carboxylic acid (57)

Prepared from KOH (4.73 g), (50) (5.9 g) after reflux overnight yielding (57) 5.54 g (99.3%). M.p. 233°–234° C.

8-Phenylthieno[2,3-b]indole-2-carboxylic acid (58)

Prepared from KOH (0.51 g), (51) (0.70 g) after reflux overnight yielding (58) 0.63 g (94%). M.p. 206°–207° C.

EXAMPLE 14

5-Chloro-8-methyl-2-morpholinocarbonylthieno[2,3-b]indole (59)

(54) (0.20 g) was dissolved in $SOCl_2$ (5 ml), DMF (1 μl) was added and the mixture was stirred 2 h at room temperature and 1 h at 50° C. The mixture was subsequently evaporated to dryness, the residue stripped with THF (10 ml) and dissolved in THF (5 ml) then morpholine (0.15 ml) was added. The mixture was stirred 2½ h at room temperature, evaporated to dryness and extracted with dichloromethane/water. The organic phase was subsequently washed with 1M NaOH and 1M HCl, dried with $MgSO_4$ and evaporated. The residue was treated with ethanol and filtered to give 0.185 g (74%) of (59). M.p. 178°–182° C.

5,8-Dimethyl-2-morpholinocarbonylthieno[2,3-b]indole (60)

(55) (0.295 g) was dissolved in $SOCl_2$ (6 ml), DMF (1 μl) was added and the mixture was stirred 2.5 h at room temperature and 0.5 h at 50° C. The mixture was subsequently evaporated to dryness, the residue stripped with toluene (10 ml) and dissolved in THF (5 ml) then morpholine (0.21 ml) was added. The mixture was stirred 1.5 h at room temperature, evaporated to dryness and extracted with dichloromethane/water. The organic phase was subsequently washed with 1M NaOH and 1M HCl, dried with $MgSO_4$ and evaporated. The residue was purified by chromatography on silical gel using toluene/ethylacetate 75/25 as eluent. The product was treated with ethanol and filtered to give 0.225 g (65%) of (60). M.p. 158°–160° C.

4,6-Dichloro-8-methyl-2-morpholinocarbonylthieno[2,3-b]indole (61)

(56) (1.00 g) was suspended in $SOCl_2$ (20 ml), DMF (1 drop) was added and the mixture was stirred 2 h at room temperature, 1 h at 50° C. and refluxed 1 h. The mixture was evaporated to dryness and dissolved in THF (15 ml) then morpholine (0.60 ml) was added. After stirring overnight the precipitate was filtered off, and recrystallized from acetic acid/water to afford 0.357 g (29%) of (61). M.p. 224°–226° C.

8-Phenyl-2-morpholinocarbonylthieno[2,3-b]indole (62)

(58) (0.44 g) was dissolved in $SOCl_2$ (3.4 ml) and stirred for 72 h. The mixture was evaporated to dryness and the residue was stripped two times with acetone (5 ml) and dissolved in acetone (10 ml). Morpholine (0.28 ml) was added and the mixture was stirred for 72 h, evaporated to dryness and extracted with dichloromethane/aqueous $NaHCO_3$ solution. The organic phase was washed with 1M NaOH and 1M HCl, evaporated to dryness and purified by chromatography on silica gel using dichloromethane/ether 1/1 as eluent. The product was recrystallized from acetic acid/water to give 0.196 g (37.7%) of (62). M.p. 162°–167° C.

7-Chloro-8-methyl-2-morpholinocarbonylthieno[2,3-b]indole (63)

(57) (0.35 g) was suspended in $SOCl_2$ (3.0 ml) and stirred for 20 h. The mixture was evaporated to dryness and the residue was stripped with toluene (10 ml) and dissolved in THF (8 ml). Morpholine (0.216 ml) was added and the mixture was stirred for 72 h, evaporated to dryness and extracted with dichloromethane/water. The organic phase was washed with 1M NaOH and 1M HCl, dried with $Na_2SO_4$ and evaporated to dryness. The crude product was recrystallized from acetic acid/water to give 0.33 g (87%) of (63). M.p. 140°–143° C.

EXAMPLE 15

Methyl 5-acetyl-8-methylthieno[2,3-b]indole-2-carboxylate (64)

To a slurry of 870 mg $AlCl_3$ in 50 ml dry 1,2-dichloroethane was added 465 µl acetyl chloride. The mixture was stirred for 30 min. at room temperature. 800 mg of (6) was added, and stirring continued overnight. Another 870 mg $AlCl_3$ and 465 µl acetyl chloride was added, and stirring continued overnight. Water was added, and the organic phase dried and evaporated to dryness giving a brown powder, which was crystallized from acetic acid and petrol ether giving (64). Yield 210 mg. M.p. 196–8° C.

EXAMPLE 16

2-Chloro-5-nitroindole-3-carbaldehyde (65)

15 g of (1) was added to a mixture of 150 ml acetic acid and 150 ml of acetic anhydride at 0°. 3.5 ml of 100% $HNO_3$ was slowly added, and after 1 hour another 3.5 ml of 100% $HNO_3$ was added. Stirring was continued for 1 hour at 0° C. The mixture was then added to ice, left in the cold overnight, and filtered to give 10 g of (65), which was used without further purification.

2-Chloro-1-methyl-5-nitroindole-3-carbaldehyde (66)

To 5 g of (65) in 100 ml THF was added 550 mg NaH and 2.5 ml methyliodide. The reaction was left with stirring overnight. Most of the THF was evaporated off, water was added, and the water phase extracted with EtOAc. The water phase was then acidified with acetic acid, which precipitated the pure product. Filtration and drying gave 770 mg of (66).

Methyl 8-methyl-5-nitrothieno[2,3-b]indole-2-carboxylate (67)

1.4 g of (66) was added to a slurry of excess $K_2CO_3$ in 100 ml of MeOH. 2 ml of methyl 2-mercaptoacetate was added and the mixture left with stirring overnight. Addition of water precipitated the product, which was washed with MeOH and water to give 640 mg of (67). M.p. 269°–71° C.

EXAMPLE 17

8-Methyl-5-nitrothieno[2,3-b]indole-2-carboxylic acid (68)

480 mg of (67) was hydrolyzed in a mixture of NaH in 25 ml of morpholine at 65° C. for 8 hours, in an attempt to directly produce the morpholino-amide. Addition of water and acidification with acetic acid precipitated (68), yield 280 mg, which was used without further purification.

8-Methyl-2-morpholinocarbonyl-5-nitrothieno[2,3-b]indole (69)

280 mg of (68) was added to 25 ml of THF, 0.5 ml of $SOCl_2$ was added, and the reaction left with stirring for 1 hour. 1 ml of morpholine was added in portions, and stirring continued. The precipitated morpholine hydrochloride was filtered off, and the solvent evaporated. The residue was purified by column chromatography on silica gel, using MeOH in $CH_2Cl_2$, 1+9 as the eluent. MeOH was added to the pooled fractions to precipitate the product, giving after filtration and drying 50 mg of (69). M.p. 250°–2° C.

EXAMPLE 18

Methyl 5-bromo-8-methylthieno[2,3]indole-2-carboxylate (70)

1.3 g N-bromosuccinimide and 1.7 g (6) was reacted in 25 ml $CH_2Cl_2$ for 30 min. Water was added, and the organic phase washed with saturated $NaHCO_3$ solution and water. Drying and evaporation gave 1.8 g of product, which was dissolved in MeOH and precipitated by adding of water. Yield 1.6 g of (70), which was used without further purification.

5-Bromo-8-methylthieno[2,3]indole-2-carboxylic acid (71)

2.5 g of (70) was hydrolyzed during 3 hours at reflux in a mixture of 25 ml 4 N NaOH and 100 ml MeOH/water 1+1. After cooling to room temperature and acidification with acetic acid the product precipitated. Filtration and drying gave 2.4 g of (71). M.p. 229°–41° C.

5-Bromo-8-methyl-2-morpholinocarbonylthieno[2,3-b]indole (72)

To 2 g of (71) in 50 ml THF was added 5 ml of $SOCl_2$, and the reaction was left with stirring overnight. Another 5 ml of $SOCl_2$ was added, and the reaction left with stirring for 3 days. The solvent was evaporated, the remanence taken up in THF and 30 ml of morpholine was added. The reaction was then left with stirring overnight. The precipitate was filtered off, and the filtrate evaporated to give 1.7 g of product, which was recrystallized in acetic acid-water, filtered and washed in MeOH to give 1.1 g of (72). M.p. 184° C.

EXAMPLE 19

8-Methylthieno[2,3-b]indole (73)

A slurry of 5 g of (9) and 650 ml of copper powder in 50 ml quinoline was heated to 200° C. for 4 hours. To the cooled reaction mixture was added 150 ml of $CH_2Cl_2$, and the mixture was washed with 1 N hydrochloric acid (3×100 ml), water (100 ml), dried and evaporated. Recrystallization from EtOH/water gave 500 mg of a byproduct, which was discarded. Addition of EtOH gave two precipitates of (73), which was combined. Yield 1.5 g. M.p. 65.5°–66.8° C.

8-Methyl-3-trifluoroacetylthieno[2,3-b]indole (74)

A mixture of 1 g of (73) and 1.1 g of 2-trifluoromethylcarbonyloxypyridine, prepared according to the literature (Keumi, T. et. al. Chem. Lett. 5 (1990) 783–6), in 25 ml of 1,2-dichloroethane, was cooled to −10° C. with stirring. 1.5 g of $AlCl_3$ was added over 15 minutes at this temperature, the reaction mixture was stirred at 0° C. for 4 hours, and at room temperature overnight. Water was added, the phases separated, and the organic phase dried and evaporated to dryness. Purification by column chromatography on silica gel in toluene gave the pure (74). Yield 590 mg. M.p. 138°–40° C.

EXAMPLE 20

3-Acetyl-2-chloroindole (75)

13.7 ml $POCl_3$ was slowly added to a mixture of dimethylacetamide (5.6 ml) in 25 ml of chloroform, at 5° C. A solution of 6.66 g of oxindole in 25 ml chloroform was slowly added, and the reaction refluxed for 7 hours, and left overnight at room temperature with stirring. The reaction mixture was added to 250 ml of ice/water, the phases separated, and the organic phase extracted with water (4×50 ml). The aqueous phases were pooled and neutralized with sodium acetate, and stirred for 4 hours at room temperature. Filtration and drying gave (75). Yield 4.8 g.

3-Acetyl-2-chloro-1-methylindole (76)

To a slurry of 310 mg of NaH in 15 ml THF was added 1 g of (75), and then 625 µl of methyl iodide. The reaction was left with stirring for 3 days. Water was added, the product extracted with diethylether, and the ether phase dried and evaporated to dryness to give (76). Yield 870 mg.

Methyl 3,8-dimethylthieno[2,3-b]indole-2-carboxylate (77)

450 µl of methyl 2-mercaptoacetate was added to a slurry of 870 mg of (76) and 1.2 g of $K_2CO_3$ in 10 ml of MeOH. The reaction was stirred overnight. 30 ml of water was added, stirring continued for 1 hour, and the product filtered off giving 160 mg of product. Recrystallization from MeOH gave 30 mg of (77). M.p. 165.5°–166.8° C.

EXAMPLE 21

2-Chloro-1-(2-methoxyethoxymethyl)indole-3-carbaldehyde (78)

1 g of (1) was dissolved in 25 ml of THF, 268 mg of NaH was added, and then 1.87 g of (2-methyloxyethyl)oxymethylchlorid. The reaction was left with stirring overnight, then added to a 2 N $K_2CO_3$ solution. The mixture was extracted with toluene, the organic phase then washed with water and brine, dried, and evaporated to give 1.5 g of oil. The oil was then extracted twice with boiling heptane, and the heptane solutions left for 2 hours to separate out a yellow oily phase. The heptane was finally decanted off, filtered, and evaporated giving 1.21 g of (78). M.p. 52.5–54° C.

Methyl 8-((2-methyloxyethyl)-oxymethyl)-thieno[2,3-b]indole-2-carboxylate (79)

400 µl of methyl 2-mercaptoacetate was added to a slurry of 1 g of (78) and 1.1 g of $K_2CO_3$ in 10 ml of MeOH. The reaction was stirred overnight, and then 20 ml of water was added. The mixture was extracted with EtOAc, and the organic layer washed with water, dried and evaporated to give (79) as a yellow oil. Yield 880 mg. $^1$H-NMR (ppm): 8.1(s, 1H); 7.8(d, 1H); 7.5(d, 1H); 7.3(m, 2H); 5.6(s, 2H); 3.9(s, 3H); 3.5(m, 4H); 3.35(s, 3H).

EXAMPLE 22

3-Acetyl-2-chloro-1-(2-methoxyethoxymethyl)indole (80)

1 g of (75) was dissolved in 25 ml THF. 250 mg NaH was added, and then 1.87 g of (2-methyloxyethyl)oxymethylchlorid. The reaction was left with stirring overnight, another 100 mg NaH was added, and the reaction continued another 4 hours. The reaction mixture was added to a 2N $K_2CO_3$ solution and extracted with toluene. The organic phase was washed with water and brine, dried and evaporated. The resulting oil was extracted twice with boiling heptane, cooled, filtered, and evaporated giving 1.23 g of (80) as a yellow oil, $^1$H-NMR (ppm): 8.35(m, 1H); 7.44(m, 1H); 7.27(m, 2H); 5.62(s, 2H); 3.58(m, 2H); 3.47(m, 2H); 3.32(s, 3H); 2.65(s, 3H).

Methyl 8-((2-methyloxyethyl)-oxymethyl)-3-methylthieno[2,3-b]indole-2carboxylate (81)

400 µl of methyl 2-mercaptoacetate was added to a slurry of 1050 mg of (80) and 1.1 g of $K_2CO_3$ in 10 ml of MeOH, and left with stirring for 48 hours. 20 ml of water was added, and the precipitate filtered off and dried. This material was thoroughly washed with pentane, filtered, dried, and recrystallized from EtOH giving 230 mg of (81) as a white powder. M.p. 85.4°–86° C.

EXAMPLE 23

1-Benzyl-2-chloro-3-acetylindole (82)

To a slurry of 400 mg of NaH in 20 ml THF was added 1 g of (75), and then 770 µl of benzyl bromide. The reaction was left with stirring for 3 days. Water was added, and the product extracted with diethylether, dried, and the solvent evaporated off to give 1.52 g of a redbrown powder, which was used without further purification.

Methyl 8-benzyl-3-methylthieno[2,3-b]indole-2-carboxylate (83)

550 µl of methyl 2-mercaptoacetate was added to a slurry of 1.45 g of (82) and 1.6 g of $K_2CO_3$ in 15 ml of MeOH, and left with stirring overnight. 30 ml of water was added, and the product isolated as a sticky lump. This lump was dissolved in EtOAc, washed with water, dried and evaporated to give an oil, which slowly solidified. Crystallization from MeOH gave (83). Yield 330 mg. M.p. 132°–4° C.

We claim:

1. A compound of formula I

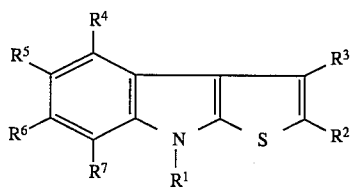

(I)

wherein $R^1$ is H; $C_{1-6}$-alkyl which is optionally substituted with halogen; $C_{2-6}$-alkenyl; $C_{2-6}$-alkynyl; $C_{3-6}$-cycloalkyl; $C_{1-4}$-alkyl which is substituted with $C_{3-6}$-cycloalkyl; carboxy; —$COR^9$; —$COOR^9$; $C_{1-4}$-alkyl substituted with dimethylamino; —$R^9$—O—$R^{10}$; —$R^9$—O—$R^{11}$; or a ring system, which comprises an aromatic group, selected from the group consisting of phenylsulfonyl, benzoyl, benzyl and phenyl, wherein the aromatic group of the ring system is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl;

$R^2$ is carboxy; cyano; nitro; —$R^9$—O—$R^{10}$; —$COOR^9$; morpholinocarbonyl; thiamorpholinocarbonyl; piperazinylcarbonyl optionally substituted with $C_{1-4}$-alkyl; a ring selected from the group consisting of tetrazolyl, oxadiazolyl and thiadiazolyl wherein the ring is optionally substituted with $C_{1-4}$-alkyl or $C_{3-6}$-cycloalkyl; methyl substituted with a morpholino group; amino unsubstituted or mono or disubstituted with a $C_{1-6}$-alkyl group; methyl which is substituted with an hydroxy or an amino group wherein the amino group is unsubstituted or N-mono or disubstituted with a $C_{1-6}$-alkyl group; or sulfamoyl unsubstituted or mono or disubstituted with a $C_{1-6}$-alkyl group; wherein the $C_{1-6}$-alkyl groups are independently optionally substituted with halogen, phenyl, benzyl, or methyl which is substituted with amino which is substituted with two methyl groups;

$R^3$ is H; $C_{1-6}$-alkyl; trifluoromethyl; trifluoroacetyl; $C_{1-6}$-alkoxy; halogen; nitro; cyano; —$COOR^9$; or amino which is unsubstituted or mono or disubstituted with $C_{1-6}$-alkyl; and $R^4$, $R^5$, $R^6$ and $R^7$ independently are H; nitro; amino; halogen; tritium; trifluoromethyl; trifluoroacetyl; sulfo; carboxy; carbamoyl; sulfamoyl; —$COR^9$; —$COOR^9$; $C_{1-6}$-alkoxy; or $C_{1-6}$-alkyl optionally substituted with halogen; or a pharmaceutically acceptable salt thereof.

2. A compound according to claim 1, wherein $R^1$ is $C_{1-6}$-alkyl optionally substituted with halogen; $C_{1-4}$-alkyl which is substituted with $C_{3-6}$-cycloalkyl; or a ring system, which comprises an aromatic group, selected from the group consisting of benzoyl, benzyl and phenyl, wherein the aromatic group is optionally substituted with $C_{1-4}$-alkyl, $C_{1-4}$-alkoxy, halogen, carboxy or nitro.

3. A compound according to claim 1, wherein $R^2$ is carboxy; cyano; morpholinocarbonyl; piperazinylcarbonyl optionally substituted with $C_{1-4}$-alkyl; a ring selected from the group consisting of tetrazolyl, oxadiazolyl and thiadiazolyl wherein the ring is optionally substituted with $C_{1-4}$-alkyl or $C_{3-6}$-cycloalkyl; methyl which is substituted with a morpholino group; amino unsubstituted or mono or disubstituted with a $C_{1-6}$-alkyl group; or methyl substituted with amino which is unsubstituted or N-mono or disubstituted with a $C_{1-6}$-alkyl group.

4. A compound according to claim 3, wherein $R^2$ is carboxy; cyano; a ring selected from the group consisting of tetrazolyl, oxadiazolyl and thiadiazolyl wherein the ring is optionally substituted with $C_{1-4}$-alkyl or $C_{3-6}$-cycloalkyl; methyl which is substituted with a morpholino group; amino unsubstituted or mono or disubstituted with a $C_{1-6}$-alkyl group; or methyl substituted with amino which is unsubstituted or N-mono or disubstituted with a $C_{1-6}$-alkyl group.

5. A compound according to claim 1, wherein $R^3$ is H; $C_{1-6}$-alkyl; trifluoromethyl; $C_{1-6}$-alkoxy; or amino which is unsubstituted or mono or disubstituted with $C_{1-6}$-alkyl.

6. The compound according to claim 1 selected from the following:
Methyl 8-benzylthieno[2,3-b]indole-2-carboxylate;
Methyl 8-methylthieno[2,3-b]indole-2-carboxylate;
Methyl 8-cyclopropylmethylthieno[2,3-b]indole-2-carboxylate;
Isopropyl 8-benzylthieno[2,3-b]indole-2-carboxylate;
Methyl thieno[2,3-b]indole-2-carboxylate;
Methyl 8-benzenesulphonylthieno[2,3-b]indole-2-carboxylate;
Methyl 8-benzoylthieno[2,3-b]indole-2-carboxylate;
Methyl 8-acetylthieno[2,3-b]indole-2-carboxylate;
Methyl 8-methyl-5-methoxythieno[2,3-b]indole-2-carboxylate;
Ethyl 8-methylthieno[2,3-b]indole-2-carboxylate;
8-Methyl-2-(3-methyl-1,2,4-oxadiazol-5-yl)thieno[2,3-b]indole;
Methyl 8-benzyl-5-bromothieno[2,3-b]indole-2-carboxylate;
Methyl 5-bromothieno[2,3-b]indole-2-carboxylate;
Methyl 5-chloro-8-methylthieno[2,3-b]indole-2-carboxylate;
Methyl 7-chloro-8-methylthieno[2,3-b]indole-2-carboxylate;
Methyl 8-phenylthieno[2,3-b]indole-2-carboxylate;
Methyl 5-methyl-8-methylthieno[2,3-b]indole-2-carboxylate;
Methyl 4,6-dichloro-8-methylthieno[2,3-b]indole-2-carboxylate;
Methyl 5-acetyl-8-methylthieno[2,3-b]indole-2-carboxylate;
Methyl 8-methyl-5-nitrothieno[2,3-b]indole-2-carboxylate;
Methyl 5-bromo-8-methylthieno[2,3]indole-2-carboxylate;
Methyl 3,8-dimethylthieno[2,3-b]indole-2-carboxylate;
Methyl 8-((2-methyloxyethyl)-oxymethyl)-thieno[2,3-b]indole-2-carboxylate;
Methyl 8-((2-methyloxyethyl)-oxymethyl )-3-meth yl thieno[2,3-b]indole-2carboxylate; or
Methyl 8-benzyl-3-methylthieno[2,3-b]indole-2-carboxylate; or a pharmaceutically acceptable salt thereof.

7. The compound according to claim 1, selected from the following:
8-Benzylthieno[2,3-b]indole-2-carboxylic acid;
8-Methylthieno[2,3-b]indole-2-carboxylic acid;
8-Benzyl-2-(5-tetrazolyl)thieno[2,3-b]indole;
8-Benzyl-5,6-dibromothieno[2,3-b]indole-2-carboxylic acid;
5-Chloro-8-methylthieno[2,3-b]indole-2-carboxylic acid;
5-Methyl-8-methylthieno[2,3-b]indole-2-carboxylic acid;
4,6-Dichloro-8-methylthieno[2,3-b]indole-2-carboxylic acid;
7-Chloro-8-methylthieno[2,3-b]indole-2-carboxylic acid;
8-Phenylthieno[2,3-b]indole-2-carboxylic acid;
8-Methyl-5-nitrothieno[2,3-b]indole-2-carboxylic acid; or
5-Bromo-8-methylthieno[2,3]indole-2-carboxylic acid; or a pharmaceutically acceptable salt thereof.

8. The compound according to claim 1 selected from the following:
8-Benzyl-2-(4-methyl-1-piperazinylcarbonyl)thieno[2,3-b]indole;

8-Benzyl-2-morpholinocarbonylthieno[2,3-b]indole;
-2-Morpholinocarbonylthieno[2,3-b]indole;
8-Methyl-2-morpholinocarbonylthieno[2,3-b]indole;
8-Methyl-2-(4-methyl-1-piperazinylcarbonyl)thieno[2,3-b]indole;
8-Methyl-2-morpholinomethylthieno[2,3-b]indole;
5-Chloro-8-methyl-2-morpholinocarbonylthieno[2,3-b]indole;
5,8-Dimethyl-2-morpholinocarbonylthieno[2,3-b]indole;
4,6-Dichloro-8-methyl-2-morpholinocarbonylthieno[2,3-b]indole;
8-Phenyl-2-morpholinocarbonylthieno[2,3-b]indole;
7-Chloro-8-methyl-2-morpholinocarbonylthieno[2,3-b]indole;
8-methyl-2-morpholinocarbonyl-5-nitrothieno[2,3-b]indole; or
5-Bromo-8-methyl-2-morpholinocarbonylthieno[2,3-b]indole; or a pharmaceutically acceptable salt thereof.

9. The compound according to claim 1 selected from the following:
8-Benzyl-2-(3-cyclopropyl-1,2,4-oxadiazol-5-yl)thieno[2,3-b]indole;
8-Benzylthieno[2,3-b]indole-2-carbonitrile; or
8-Benzyl-2-hydroxymethylthieno[2,3-b]indole; or a pharmaceutically acceptable salt thereof.

10. A compound of formula I

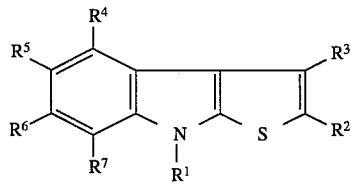

(I)

wherein $R^1$ is $C_{2-6}$-alkenyl; $C_{2-6}$-alkynyl; $C_{3-6}$-cycloalkyl; $C_{1-4}$-alkyl substituted with $C_{3-6}$-cycloalkyl; carboxy; —$COR^9$; —$COOR^9$; $C_{1-4}$-alkyl substituted with dimethylamino; —$R^9$—O—$R^{10}$; —$R^9$—O—$R^{10}$—O—$R^{11}$ or a ring system, which comprises an aromatic group, selected from the group consisting of phenylsulfonyl, benzoyl, benzyl and phenyl, wherein the aromatic group is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl;

$R^2$ is carbamoyl unsubstituted or mono or disubstituted with a $C_{1-6}$-alkyl group wherein the $C_{1-6}$-alkyl group is independently optionally substituted with halogen, phenyl, benzyl or methyl which is substituted with amino which is substituted with two methyl groups;

$R^3$ is H; $C_{1-6}$-alkyl; trifluoromethyl; trifluoroacetyl; $C_{1-6}$-alkoxy; halogen; nitro; cyano; —$COOR^9$; or amino unsubstituted or mono or disubstituted with $C_{1-6}$-alkyl; and $R^4$, $R^5$, $R^6$ and $R^7$ independently are H; nitro; amino; halogen; tritium; trifluoromethyl; trifluoroacetyl; sulfo; carboxy; carbamoyl; sulfamoyl; —$COR^9$; —$COOR^9$; $C_{1-6}$-alkoxy; or $C_{1-6}$-alkyl optionally substituted with halogen; or a pharmaceutically acceptable salt thereof.

11. A compound according to claim 10, wherein $R^1$ is $C_{1-4}$-alkyl substituted with $C_{3-6}$-cycloalkyl; or a ring system, which comprises an aromatic group, selected from the group consisting of benzoyl, benzyl and phenyl, wherein the aromatic group is optionally substituted with $C_{1-4}$-alkyl, $C_{1-4}$-alkoxy, halogen, carboxy or nitro.

12. A compound according to claim 10, wherein $R^1$ is —$COR^9$; —$COOR^9$; or a ring system, which comprises an aromatic group, selected from the group consisting of benzoyl, benzyl and phenyl, wherein the aromatic group is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl; and $R^2$ is unsubstituted carbamoyl.

13. A compound according to claim 10, wherein $R^2$ is carbamoyl mono or disubstituted with a $C_{1-6}$-alkyl group wherein the $C_{1-6}$-alkyl group is independently optionally substituted with halogen, phenyl, benzyl or methyl which is substituted with amino which is substituted with two methyl groups.

14. A compound according to claim 10, wherein $R^3$ is H; $C_{1-6}$-alkyl; trifluoromethyl; $C_{1-6}$-alkoxy; or amino which is unsubstituted or mono or disubstituted with $C_{1-6}$-alkyl.

15. The compound according to claim 10 selected from the following:
8-Benzylthieno[2,3-b]indole-2-carboxamide;
8-Benzylthieno[2,3-b]indole-2-(N-(N',N'-dimethyl)-3-aminopropyl)carboxamide;
8-Benzylthieno[2,3-b]indole-2-(N-(N',N'-dimethyl)-3-aminopropyl-N-methylcarboxamide); or
8-Benzylthieno[2,3-b]indole-2-N-ethylcarboxamide; or a pharmaceutically acceptable salt thereof.

16. A compound of formula I

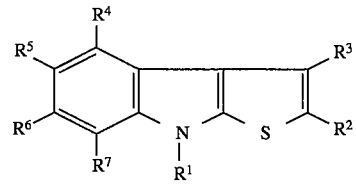

(I)

wherein $R^1$ is $C_{1-6}$-alkyl optionally substituted with halogen;

$R^2$ is carbamoyl mono or disubstituted with a $C_{1-6}$-alkyl group wherein the $C_{1-6}$-alkyl group is independently optionally substituted with halogen, phenyl, benzyl or methyl which is substituted with amino which is substituted with two methyl groups;

$R^3$ is H; $C_{1-6}$-alkyl; trifluoromethyl; trifluoroacetyl; $C_{1-6}$-alkoxy; halogen; nitro; cyano; —$COOR^9$; or amino unsubstituted or mono or disubstituted with $C_{1-6}$-alkyl; and $R^4$, $R^5$, $R^6$ and $R^7$ independently are H; nitro; amino; halogen; tritium; trifluoromethyl; trifluoroacetyl; sulfo; carboxy; carbamoyl; sulfamoyl; —$COR^9$; —$COOR^9$; $C_{1-6}$-alkoxy; or $C_{1-6}$-alkyl optionally substituted with halogen; or a pharmaceutically acceptable salt thereof.

17. The compound according to claim 16 selected from the following:
8-Methylthieno[2,3-b]indole-2-(N-methylcarboxamide);
8-Methylthieno[2,3-b]indole-2-(N,N-dimethylcarboxamide); or
8-Methylthieno[2,3-b]indole-2-(N-phenylcarboxamide); or pharmaceutically acceptable salt thereof.

18. A pharmaceutical composition comprising a pharmaceutically acceptable carrier or diluent and a compound of formula I

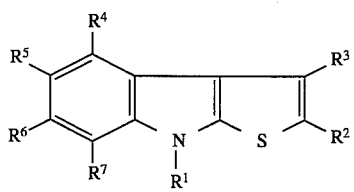

wherein
- $R^1$ is H; $C_{1-6}$-alkyl optionally substituted with halogen; $C_{2-6}$-alkenyl; $C_{2-6}$-alkynyl; $C_{3-6}$-cycloalkyl; $C_{1-4}$-alkyl substituted with $C_{3-6}$-cycloalkyl; carboxy; —$COR^9$; —$COOR^9$; $C_{1-4}$-alkyl substituted with dimethylamino; —$R^9$—O—$R^{10}$; —$R^9$—O—$R^{10}$—O—$R^{11}$; or a ring system, which comprises an aromatic group, selected from the group consisting of phenylsulfonyl, benzoyl, benzyl and phenyl, wherein the aromatic group is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl;
- $R^2$ is carboxy; cyano; nitro; —$R^9$—O—$R^{10}$; —$COOR^9$; morpholinocarbonyl; thiamorpholinocarbonyl; piperazinylcarbonyl optionally substituted with $C_{1-4}$-alkyl; a ring selected from the group consisting of tetrazolyl, oxadiazolyl and thiadiazolyl wherein the ring is optionally substituted with $C_{1-4}$-alkyl or $C_{3-6}$-cycloalkyl; morpholinomethyl; amino unsubstituted or mono or disubstituted with a $C_{1-6}$-alkyl group; methyl substituted with amino which is unsubstituted or N-mono or disubstituted with a $C_{1-6}$-alkyl group; sulfamoyl unsubstituted or mono or disubstituted with a $C_{1-6}$-alkyl group; or carbamoyl unsubstituted or mono or disubstituted with a $C_{1-6}$-alkyl group; wherein the $C_{1-6}$-alkyl group(s) is/are independently optionally substituted with halogen, phenyl, benzyl or methyl which is substituted with amino which is substituted with two methyl groups;
- $R^3$ is H; $C_{1-6}$-alkyl; trifluoromethyl; trifluoroacetyl; $C_{1-6}$-alkoxy; halogen; nitro; cyano; —$COOR^9$; or amino unsubstituted or mono or disubstituted with $C_{1-6}$-alkyl; and
- $R^4$, $R^5$, $R^6$ and $R^7$ independently are H; nitro; amino; halogen; tritium; trifluoromethyl; trifluoroacetyl; sulfo; carboxy; carbamoyl; sulfamoyl; —$COR^9$; —$COOR^9$; $C_{1-6}$-alkoxy; or $C_{1-6}$-alkyl optionally substituted with halogen; or a pharmaceutically acceptable salt thereof.

19. A pharmaceutical composition according to claim 18 in the form of an oral dosage unit or parenteral dosage unit.

20. A pharmaceutical composition according to claim 19, wherein said dosage unit comprises from about 1 to about 100 mg of the compound.

21. A pharmaceutical composition according to claim 18, wherein $R^2$ is carbamoyl unsubstituted or mono or disubstituted with a $C_{1-6}$-alkyl group wherein the $C_{1-6}$-alkyl group is independently optionally substituted with halogen, phenyl, benzyl or methyl which is substituted with amino which is substituted with two methyl groups.

22. A method of treating a disease in the central nervous system related to the metabotropic glutamate receptor system comprising administering to a subject in need thereof an effective amount of a compound of formula I

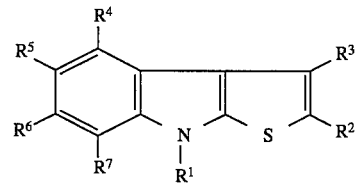

wherein
- $R^1$ is H; $C_{1-6}$-alkyl optionally substituted with halogen; $C_{2-6}$-alkenyl; $C_{2-6}$-alkynyl; $C_{3-6}$-cycloalkyl; $C_{1-4}$-alkyl substituted with $C_{3-6}$-cycloalkyl; carboxy; —$COR^9$; —$COOR^9$; $C_{1-4}$-alkyl substituted with dimethylamino; —$R^9$—O—$R^{10}$; —$R^9$—O—$R^{10}$—O—$R^{11}$; or a ring system, which comprises an aromatic group, selected from the group consisting of phenylsulfonyl, benzoyl, benzyl and phenyl, wherein the aromatic group is optionally substituted with $C_{1-4}$-alkyl, $C_{1-4}$-alkoxy, halogen, carboxy or nitro, wherein $R^9$, $R^{10}$ and $R^{11}$ are independently $C_{1-6}$-alkyl;
- $R^2$ is H; carboxy; cyano; nitro; $C_{1-6}$-alkyl optionally substituted with hydroxy; —$R^9$—O—$R^{10}$; —$COOR^9$; morpholinocarbonyl; thiamorpholinocarbonyl; piperazinylcarbonyl optionally substituted with $C_{1-4}$-alkyl; a ring selected from the group consisting of tetrazolyl, oxadiazolyl and thiadiazolyl wherein the ring is optionally substituted with $C_{1-4}$-alkyl or $C_{3-6}$-cycloalkyl; morpholinomethyl; amino unsubstituted or mono or disubstituted with a $C_{1-6}$-alkyl group; methyl substituted with amino which is unsubstituted or N-mono or disubstituted with a $C_{1-6}$-alkyl group; sulfamoyl unsubstituted or mono or disubstituted with a $C_{1-6}$-alkyl group; or carbamoyl unsubstituted or mono or disubstituted with a $C_{1-6}$-alkyl group; wherein the $C_{1-6}$-alkyl group(s) is/are independently optionally substituted with halogen, phenyl, benzyl, or methyl which is substituted with amino which is substituted with two methyl groups;
- $R^3$ is H; $C_{1-6}$-alkyl; trifluoromethyl; trifluoroacetyl; $C_{1-6}$-alkoxy; halogen; nitro; cyano; —$COOR^9$; or amino unsubstituted or mono or disubstituted with $C_{1-6}$-alkyl; and
- $R^4$, $R^5$, $R^6$ and $R^7$ independently are H; nitro; amino; halogen; tritium; trifluoromethyl; trifluoroacetyl; sulfo; carboxy; carbamoyl; sulfamoyl; —$COR^9$; —$COOR^9$; $C_{1-6}$-alkoxy; or $C_{1-6}$-alkyl optionally substituted with halogen; or a pharmaceutically acceptable salt thereof.

23. The method according to claim 22, wherein the disease is epilepsy, senile dementia, Parkinson's disease, Huntington's Chorea, pain, and cerebral ischemia.

* * * * *